US009091590B2

(12) United States Patent
Vance (10) Patent No.: US 9,091,590 B2
(45) Date of Patent: Jul. 28, 2015

(54) MAGNETO-OPTIC DISPERSION SPECTROMETER (71) Applicant: Joseph Daniel Vance, Scotts Valley, CA (US)

(72) Inventor: Joseph Daniel Vance, Scotts Valley, CA (US)

(*) Notice: Subject to any disclaimer, the term of this patent is extended or adjusted under 35 U.S.C. 154(b) by 264 days.

(21) Appl. No.: 13/728,907

(22) Filed: Dec. 27, 2012

(65) Prior Publication Data

US 2013/0208276 A1 Aug. 15, 2013

Related U.S. Application Data (60) Provisional application No. 61/580,656, filed on Dec. 28, 2011.

(51) Int. Cl.
G01J 3/28 (2006.01)
G01J 3/02 (2006.01)
G01N 21/31 (2006.01)
G01N 21/17 (2006.01)

(52) U.S. Cl.
CPC . G01J 3/02 (2013.01); G01N 21/31 (2013.01); G01N 2021/1793 (2013.01)

(58) Field of Classification Search
CPC .................................. G01J 3/28; G01J 3/447
USPC ........................................................ 356/327
See application file for complete search history.

(56) References Cited

U.S. PATENT DOCUMENTS

| 5,094,530 | A | 3/1992 | Rogasch |
| 5,181,077 | A | 1/1993 | Dencks |
| H1844 | H | 3/2000 | Billmers |
| 7,876,445 | B1 * | 1/2011 | Vance ........................ 356/453 |
| 8,605,282 | B2 * | 12/2013 | Groswasser ............... 356/367 |
| 2005/0179905 | A1 * | 8/2005 | Ohtake et al. ............. 356/450 |
| 2011/0001979 | A1 * | 1/2011 | Vance ........................ 356/453 |
| 2011/0007307 | A1 * | 1/2011 | Vance ........................ 356/301 |

OTHER PUBLICATIONS

Chen, H.,et al., "Sodium-vapor dispersive Faraday filter", Optics Letters, Jun. 15, 1993, pp. 1019-1021, vol. 15, No. 5.
Pochi Yeh, "Dispersive magnetooptic filters", Applied Optics, vol. 21, No. 11, pp. 2069-2075, Jun. 1, 1982.

* cited by examiner

Primary Examiner — Roy M Punnoose (57) ABSTRACT

A method and apparatus is disclosed for measurement of probe light frequency. The apparatus includes an optical spectrometer comprised of a medium of rapidly changing circular birefringence. The circular birefringent medium changes the polarization of probe light an amount that is dependent upon probe light frequency. Thus probe light frequency is deduced by analyzing probe light polarization after it propagates through the birefringent medium. The birefringent medium is constructed from a gaseous substance and a magnetic field, where the gaseous substance has one or more absorption lines near the probe light frequency. The magnetic field permeates the gaseous substance and shifts the frequency of the absorption line(s) by the Zeeman effect. The method includes probe light emitted from a transmitter, which scatters off of a target, then the scattered probe light is collected and transmitted through the optical spectrometer where frequency is measured. With measurement of probe light frequency, a variety of information about the target can be deduced.

2 Claims, 8 Drawing Sheets

MAGNETO-OPTIC DISPERSION SPECTROMETER

This application claims benefit of priority to U.S. Provisional Patent Application Ser. No. 61/580,656 filed on Dec. 28, 2011.

FIELD OF THE INVENTION

This invention relates to optical spectrometers utilizing circular birefringence to rotate the linear polarization of light, and more particularly to deducing the photon wavelength based on an analysis of light polarization after propagating light through the circularly birefringent medium.

BACKGROUND OF THE INVENTION

High resolution measurement of light frequency or wavelength typically makes use of comparing photon wavelength to another object. One method is to compare the wavelength of light to a physical length, such as the cavity length of a Fabry Perot interferometer. Another method is to compare photon wavelength to the wavelength of other photons, called heterodyne detection. A third method is to compare the energy of a photon, which is proportional to frequency, to an absorption line. A new method is introduced here that measures photon wavelength by an absorption line that relies upon dispersion, which accompanies absorption, of an absorption line.

DETAILED DESCRIPTION OF THE INVENTION

Several drawings illustrate physical the attributes of a magneto-optic dispersion spectrometer, and quantities that may be manifested with its construction, in accordance with embodiments of the present invention. Examples are described that have particular absorbing substances, mediums, transitions, wavelengths of complimentary light pairs, etc. for purposes of illustration. However, it should be noted that the choices of particular absorbing substance and particular transitions are abundant. Also, while concomitant to the chosen transitions, the wavelengths of the probe light have wide latitude of choice upon a continuum. Thus it is recognized that the apparatus and means described herein may vary without departing from the basic underlying concepts of the invention.

The current invention is an optical spectrometer based on dispersion from absorption. A high resolution optical spectrometer measures some property of light as a function of frequency, to determine frequency. The current invention utilizes a rapidly changing electric susceptibility to demarcate frequency. Embodiments of the current invention are based the creation of a medium where in selected frequency regions the dispersion changes rapidly due to absorption.

Consider an absorbing substance such as an atomic vapor, which has many energy states. With the absorption of a photon, a transition occurs from a lower energy state to a higher energy state. Not only energy is conserved in the transition, but momentum as well. Since photons have an angular momentum of $\hbar$, conservation of angular momentum requires that there must be a difference of $\hbar$ angular momentum between the higher energy state and the lower energy state. When there is a difference of zero or $2\hbar$ angular momentum between the higher energy state and lower energy state, the absorption of two photons will satisfy conservation of angular momentum. This distinguishes two-photon absorption processes from single photon absorption processes: In a single photon absorption process, the difference between highest and lowest states of the absorbing substance, of energy and angular momentum, matches a single photon. In a two-photon absorption process, the difference of energy between highest and lowest states is the sum of energy contained in two photons, and the difference in angular momentum between highest and lowest states is the vector sum of the angular momentum from two photons.

The atom or molecule will absorb a photon only if the energy of the photon matches the energy of the transition. An absorption line is a frequency bandwidth of light that can be absorbed by a substance. When light is of the correct wavelength, having the same energy as the transition energy, there is resonance absorption. For example, $^{87}$Rb has many absorption lines, two of which are near a wavelength of 780.4 nm and are separated by about 9 GHz.

Preferential absorption or resonance absorption also affects light phase, or dispersion. The electric susceptibility is used to describe both the absorption and dispersion effects. The real portion of the electric susceptibility affects light phase while the imaginary portion of the susceptibility quantifies absorption. Whenever the real portion electric susceptibility is different for each circular polarization states of linear polarized light, then the medium becomes circularly birefringent. Linear polarized light will undergo polarization rotation to another linear polarized state while traveling through a circular birefringent medium. When the imaginary portion of the susceptibility is different for each circular polarization of linear polarized light, then linear polarized light will be transformed into elliptically polarized light.

To quantify the birefringence, the electric susceptibility can be used and is defined here in terms of dielectric polarization density:

$$\vec{P} = \epsilon_o \chi \vec{E} \quad \text{Equation 1}$$

Where the electric susceptibility $\chi$ is the proportionality constant linking the electric field of the probe light to the dielectric polarization, and $\epsilon_o$ is the permittivity of free space. The electric susceptibility $\chi$ is dimensionless and also a complex quantity, and is expressed in component form as:

$$\chi = \chi' + i\chi'' \quad \text{Equation 2}$$

Using a circular polarization basis to express linear light, with some minor approximations and removing time dependence, the electric field of light after traveling a distance/within a resonance absorption medium is:

$$\vec{E}(l) = -\frac{E_o}{\sqrt{2}} \exp\left[i\left\{\frac{\omega}{c}\left(1 + \frac{\chi'_+}{2} + i\frac{\chi''_+}{2}\right)l\right\}\right] \hat{x} \quad \text{Equation 3}$$
$$+ \frac{E_o}{\sqrt{2}} \exp\left[i\left\{\frac{\omega}{c}\left(1 + \frac{\chi'_-}{2} + i\frac{\chi''_-}{2}\right)l\right\}\right] \hat{z}$$

Where $\omega$ is the angular frequency and c is the speed of light. Equation (3) demonstrates that $\chi'$, the real portion of the electric susceptibility, affects phase, while $\chi''$, the imaginary portion of the electric susceptibility, is related to absorption. The subscripts, plus and minus, attached to the susceptibilities identifies to which circular polarization state the electric susceptibility applies to: right and left handed polarization, respectively. Notice that the field vector is written in a circular polarization basis.

Figure 1:
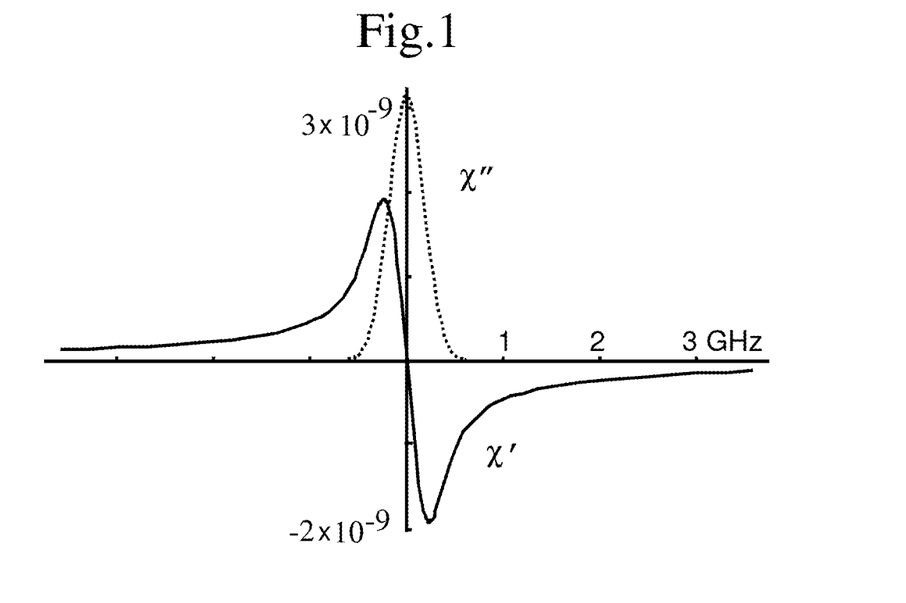
FIG. 1 shows the real ($\chi'$) and imaginary ($\chi''$) portions of the electric susceptibility near an absorption line.

The susceptibility is an analytic function. This has implications to the relationship of the real and imaginary portions of the susceptibility. The real and imaginary portions of the susceptibility are inexorably linked. In fact, if one is known then the other can be derived from it. Thus absorption can't be suppressed without also suppressing dispersion. FIG. 1 is an example of the real and imaginary susceptibility from an absorption line. The region where the real portion of susceptibility changes most rapidly with frequency is also the region where absorption occurs, and where the susceptibility is useful for a spectrometer. Absorption destroys the linear polarization property of the light, so the amount of absorption must be limited.

Figure 2:
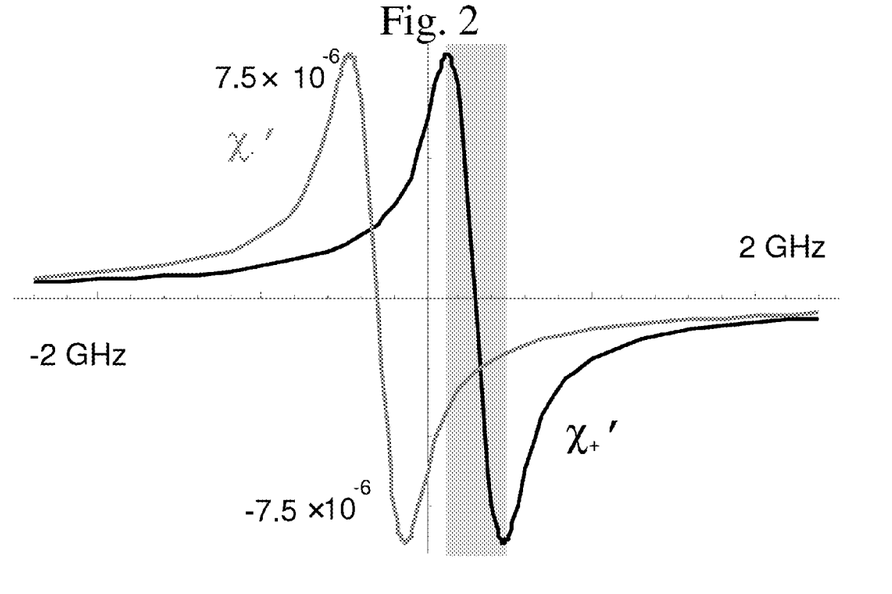
FIG. 2 shows the real ($\chi'$) portion of the susceptibility for each circular polarization component of the linearly polarized probe light when there is an applied longitudinal magnetic field. One of the frequency regions where the spectrometer is capable of measurement is shaded in gray.

The susceptibility for each circular component of resonance absorption light is typically the same. In a circular birefringent medium, the susceptibilities for each circular polarization component of the probe light are different. A longitudinal magnetic field that permeates the substance will shift up the frequency of resonance for one circular component of light, and shift down in the frequency of resonance for the other circular component of light. The magnetic field induces a difference in susceptibility making the medium birefringent. FIG. 2 shows the real portion of the susceptibility of rubidium when there is an applied magnetic field. The imaginary portion is not shown but is non-negligible in the regions where the real portion of the susceptibility crosses zero. The spectral area in gray spans one of the regions of where the magneto-optic dispersion spectrometer is used for frequency measurement. Alternatively, the other region where the susceptibility crosses zero could be used to build a spectrometer.

Figure 3:
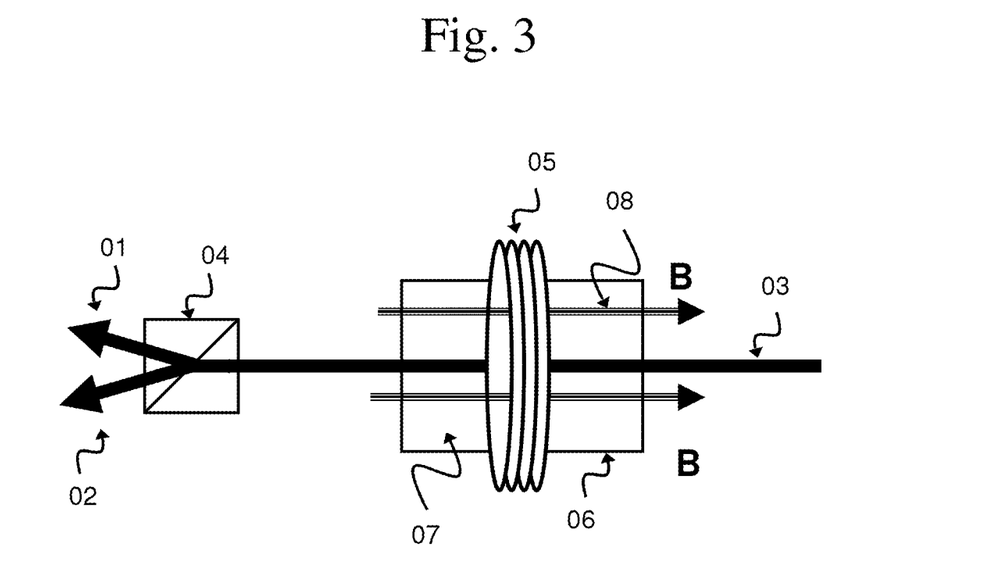
FIG. 3 is a schematic diagram of the magneto-optic dispersion spectrometer in accordance with one embodiment of the present invention.

Applying the above concepts we can begin to explain the present invention. FIG. 3 illustrates the major components that operate as a magneto-optic dispersion spectrometer, in accordance with one embodiment of the present invention. An absorbing substance 07 is contained in cell 06. For example cell 06 may be a transparent vessel that contains rubidium, some of which will be in a vapor state. Atomic vapors are not the only appropriate absorbing substance 07. Another example of an absorbing substance 07 is molecular oxygen, $O_2$. If the absorbing substance 07 is a solid, cell 06 may be unnecessary. A heater and a temperature controller may be implemented to control the temperature of the absorbing substance 07. An example of absorbing substance 07 and single photon absorption process is $5S_{1/2} \rightarrow 5P_{3/2}$ transition of rubidium with photon wavelength of 780.4 nm. The probe light 03 may be in a known predominately linear polarized state. It may be desirable to propagate the probe light 03 through a linear polarizer to remove some background light and to purify the polarization of the probe light 03. Then the probe light 03 is propagated through the absorbing substance 07. A longitudinal magnetic field 08 produced by magnet 05 permeates the absorbing substance 07 and shifts absorption line frequency up for one circular polarization component of the probe light 03 and shifts the absorption line frequency down for the other circular polarization component of the probe light 03. Longitudinal refers to the direction of the magnetic field 08 relative to the direction of travel of probe light 03. A longitudinal magnetic field 08 has a direction that is approximately the same, or approximately opposite, the propagation direction of probe light 03. The absorption substance 07 and magnetic field 08 combine to create a birefringent medium that changes rapidly as a function of frequency. After traveling through the birefringent medium, the probe light 03 will have polarization state that is dependent upon its frequency. To determine probe light 03 frequency from its polarization state, a polarizing beam splitter 04 may be used. A polarizing beam splitter, such as a Wollaston prism, accepts light and splits its direction of travel into a first beam and a second beam. The first beam will be predominately of a particular linear polarization, and the second beam will be predominately of another linear polarization that is orthogonal to the first beam.

Probe light 03 enters the polarizing beam splitter 04 and is split into a first linear polarization component 01 and a second linear polarization component 02. The relative magnitude of the first beam to the second beam is then used to determine probe light 03 frequency.

Figure 4:
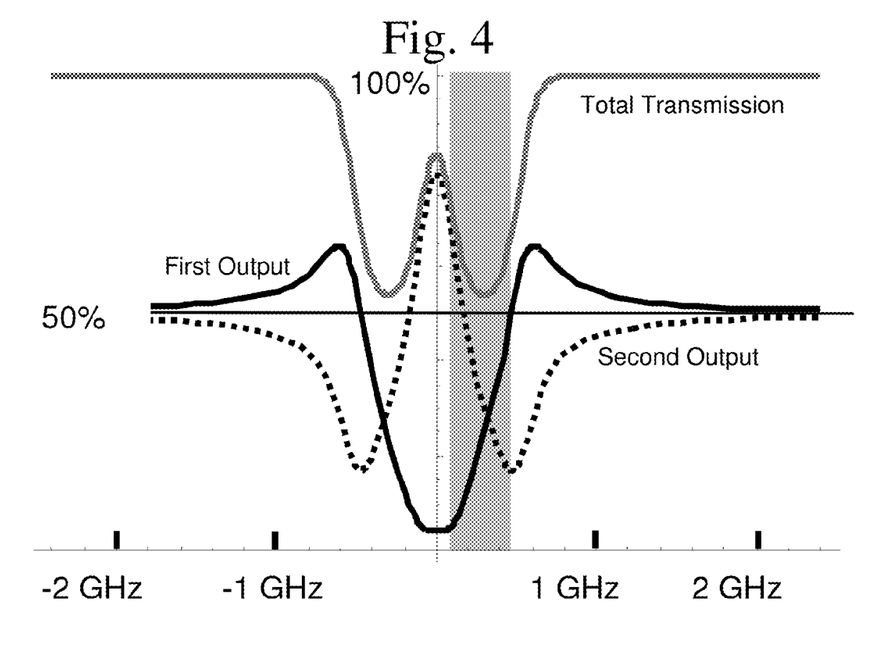
FIG. 4 is a plot of transmission spectra into two separate channels, a first linear polarization component and second linear polarization component after traveling through a polarizing beam splitter oriented 45 degrees relative to probe light initial polarization. The ratio of the components can be used to deduce the probe light frequency in accordance with one embodiment of the present invention. One of the frequency regions where the spectrometer is capable of measurement is shaded in gray.
Figure 5:
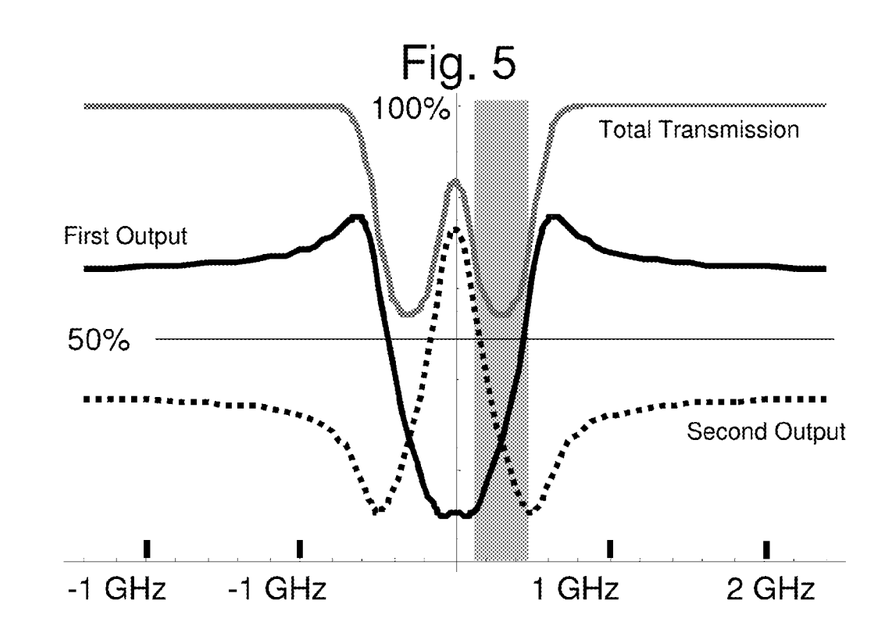
FIG. 5 is a plot of transmission spectra into two separate channels, a first linear polarization component and second linear polarization component after traveling through a polarizing beam splitter oriented 53 degrees relative to probe light initial polarization. The ratio of the components can be used to deduce the probe light frequency, in accordance with one embodiment of the present invention. One of the frequency regions where the spectrometer is capable of measurement is shaded in gray.

Since the difference in the real portion of the susceptibilities for each circular polarization state in the effective region shown in FIG. 2 is predominately of one sign, a 45 degree orientation of the polarizing beam splitter relative to the initial polarization of probe light 03 may not be optimum. FIG. 4 shows transmission paths through the polarizing beam splitter 04 with an orientation of 45 degrees relative to initial probe light 03 polarization. FIG. 5 shows the transmission paths through the polarizing beam splitter 04 with an orientation of 53 degrees relative to initial probe light 03 orientation. The transmission spectrum of FIG. 5 has more symmetry than transmission spectrum of FIG. 4. However, if there is background light it may be more advantageous to use a beam splitter orientation at 45 degrees and corresponding asymmetric transmission like that shown in FIG. 4.

The probe light 03 travels through the circularly birefringent medium, the polarization of the light will be rotated an amount and direction depending upon its frequency. So the probe light 03 light will preferentially choose one particular transmission path through the polarizing beam splitter 04; first linear polarization component 01 or second linear polarization component 02, depending upon its frequency. Mathematically, the transmission into each channel through the polarizing beam splitter 04 is described in the following paragraph.

Define a coordinate system with $\hat{z}$ axis assigned to the propagation direction, and $\hat{x}$ assigned to the polarization direction of probe light 03 before it enters the cell 06 for the first time. If the polarizing beam splitter 04 is oriented at an angle of $\theta$, relative to $\hat{x}$, the first linear polarization component 01 and second linear polarization component 02 polarization directions can be expressed as $\hat{x}\cos\theta \pm \hat{y}\sin\theta$ respectively. The transmission of probe light 03 into first linear polarization component 01 and second linear polarization component 02 will be:

$$T = \frac{\left|\vec{E}\cdot(\hat{x}\cos\theta \pm \hat{y}\sin\theta)\right|^2}{E_o^2} \quad \text{Equation 4}$$

$$T = \frac{1}{4}\begin{bmatrix} \exp\left(-\frac{\omega}{c}\chi_u''l\right) + \exp\left(-\frac{\omega}{c}\chi_d''l\right) \pm \\ 4\cos\theta\sin\theta\exp\left(-\frac{\omega}{c}\frac{\chi_u'' + \chi_d''}{2}l\right)\sin\left(\frac{\omega}{c}\frac{\chi_u' - \chi_d'}{2}l\right) \pm \\ 2(\cos^2\theta - \sin^2\theta)\exp\left(-\frac{\omega}{c}\frac{\chi_u'' + \chi_d''}{2}l\right)\cos\left(\frac{\omega}{c}\frac{\chi_u' - \chi_d'}{2}l\right) \end{bmatrix} \quad \text{Equation 5}$$

where the subscripts u and d on the susceptibilities refer to susceptibility from the up shifted frequency absorption line and down shifted frequency absorption line respectively. The plus/minus sign refers to first linear polarization component 01 or second linear polarization component 02 respectively. The angle of the Wollastan prism is represented as $\theta$. If the signal magnitude of the first linear polarization component 01 is divided by the signal magnitude of the second linear polarization component 02, the ratio can be used to determine the frequency of the light.

Notice that absorption is also plotted in both FIG. 4 and FIG. 5. When absorption is small, there is not much dispersion. If absorption is too large, then all of one circular component of the probe light 03 is absorbed. When too much of one circular component is attenuated, the probe light 03 becomes elliptically polarized and no longer operates as a spectrometer. The absorption shown in FIG. 4 and FIG. 5 is near optimum for high resolution. The spectrometer still works well when a majority of one component of the probe light 03 is absorbed.

Figure 6:
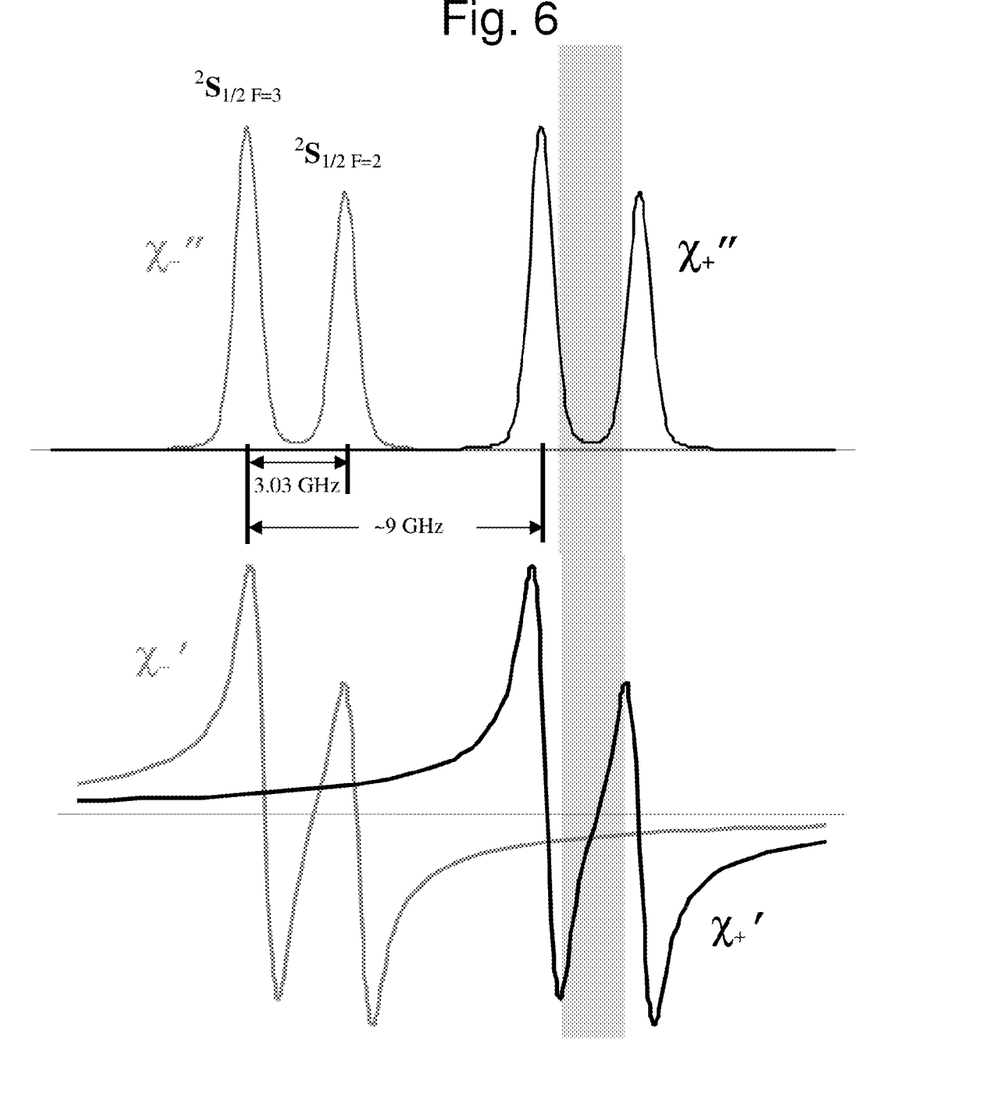
FIG. 6 is a plot of the susceptibility for $^{85}$Rb that has a longitudinal magnetic field applied to it. One of the frequency regions where the spectrometer is capable of measurement is shaded in gray.
Figure 7:
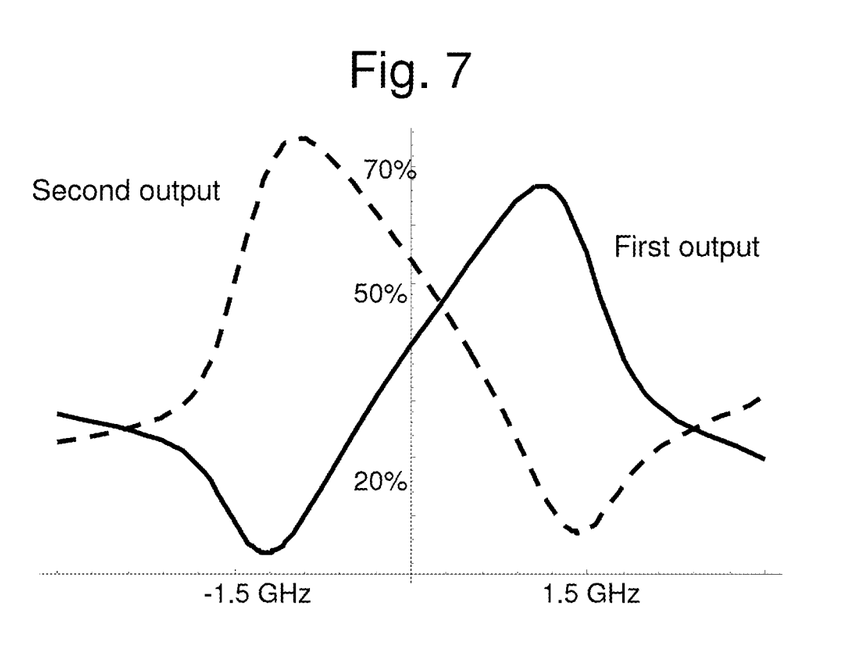
FIG. 7 is a plot of transmission spectra of $^{85}$Rb into two separate channels, a first linear polarization component and second linear polarization component after traveling through a polarizing beam splitter oriented 45 degrees relative to probe light initial polarization. The ratio of the components can be used to deduce the probe light frequency in accordance with one embodiment of the present invention.

Another embodiment of the present invention is improved by nature providing multiple absorption lines, close in frequency proximity. One such example is $^{85}$Rb, which has a hyperfine splitting of the ground state. The $D_2$ line of $^{85}$Rb is actually two distinct lines separated by 3.036 GHz. In this embodiment, $^{85}$Rb is contained in cell 6 of FIG. 3. instead of $^{87}$Rb. When a magnetic field Zeeman splitting shifts both of the absorption lines. The susceptibility for $^{85}$Rb that is shifted by approximately 1800 Gauss is shown in FIG. 6. In between the absorption lines in the shaded region is one of the two frequency bandwidths where the spectrometer operates with negligible absorption.

Figure 8:
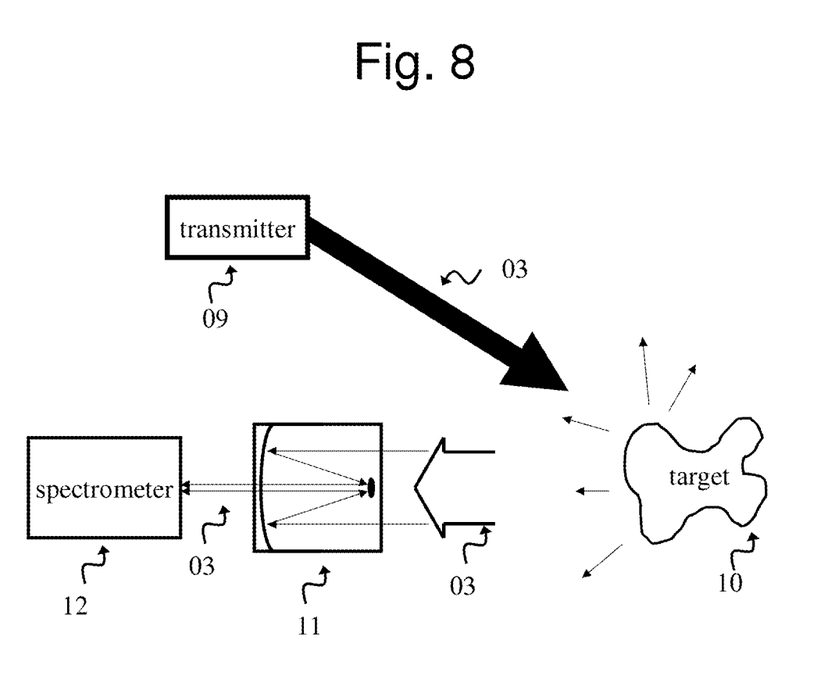
FIG. 8 is a schematic diagram of a remote sensing system that utilizes the magneto-optic dispersion spectrometer in accordance with one embodiment of the present invention.

The magneto-optic dispersion spectrometer can be used as a component of a remote sensing system. FIG. 8 shows a remote sensing system where a transmitter 09 emits probe light 03. The probe 03 light is incident upon a target 10 where it is scattered. The target may be some hard object such as an aircraft, or it may be a distributed medium such as the atmosphere or ocean. Some of the scattered probe light 03 is collected by a telescope 11 that directs it to the magneto-optic dispersion spectrometer 12. Information such as wind speed, wind sheer & turbulence may be deduced by measuring how much the scattered probe light 03 is Doppler shifted. Range may also be deduced by using a transmitter 09 that emits continuous wave light that is frequency modulated.

The scattering process may change the distribution of frequencies that constitute the probe light 03. If the scattering distribution is quantified, then atmospheric state variables can be computed. The magneto-optic dispersion spectrometer 12 may be used to the recover the distribution shape of the scattered probe light 03. Consider that probe light 03 that is emitted from a transmitter and then is scattered off of some object that changes the frequency distribution. Further consider that each first linear polarization component 01 and second linear polarization component 02 are an integration of the distribution of probe light 03 multiplied by the transmission (probability of capture) into a particular component, integrated over frequency. If the probe light 03 is frequency scanned, then signals at each first linear polarization component 01 and second linear polarization component 02 at a particular location along the scan represent an integration or transform over a different portion of the distribution. The frequency distribution of scattered probe light 03 can then be recovered by comparison of transforms obtained at different frequency locations as scanning occurs, to transforms from known beam shape at each of those different frequency locations. The scattered probe light 03 may have a distribution of frequencies that is a composite of more than one type of scattering process. Mie scattering off of aerosol particles will have a different distribution than Rayleigh scattering which is scattering off of molecules. The magneto-optic dispersion spectrometer may be used to resolve the different scattering processes. For instance, if the Rayleigh scattering is quantified, then the atmospheric state variables of temperature and pressure can be computed.

The magneto-optic dispersion spectrometer may be used to demodulate information from frequency modulated laser beams. A laser communication system can be built by frequency modulating information into the probe light 03 and transmitting it to a receiver containing a magneto-optic dispersion spectrometer to decode the information.

In the above descriptions, numerous details are set forth. It will be apparent, however, to one skilled in the art, that the present invention may be practiced without these specific details. In some instances, well-known structures and devices are shown in block diagram form, rather than in detail, in order to avoid obscuring the present invention. It is to be understood that the above descriptions are intended to be illustrative, and not restrictive. Many other embodiments will be apparent to those of skill in the art upon reading and understanding the above description. The scope of the invention should, therefore, be determined with reference to the appended claims, along with the full scope of equivalents to which such claims are entitled.

What is claimed is:

1. An optical spectrometer, acting upon probe light, comprising:

(a) an absorbing substance with one or more absorption lines;

(b) a longitudinal magnetic field permeating the absorbing substance;

(c) a polarizing beam splitter;

wherein absorption of the absorbing substance is associated with a transition from a ground state to an excited state of the absorbing substance;

wherein the absorbing substance and the longitudinal magnetic field combine to form a birefringent medium for the probe light;

wherein the probe light propagates through the birefringent medium and then is transmitted through the polarizing beam splitter;

wherein the birefringent medium changes the polarization of the probe light an amount that is dependent upon probe light frequency;

wherein the polarizing beam splitter splits the probe light into a first linear polarization component and a second linear polarization component;

wherein the angular orientation of the polarizing beam splitter relative to the probe light polarization axis is such that the first linear polarization component emerging from the polarizing beam splitter is not an orthogonal component relative to the original polarization orientation of the probe light;

wherein the angular orientation of the polarizing beam splitter relative to the original probe light polarization axis is such that the second linear polarization component emerging from the polarizing beam splitter is not an orthogonal component relative to the original polarization orientation of the probe light;

and probe light frequency is determined from the relative magnitude of the first linear polarization component to the second linear polarization component;

wherein probe light absorption occurs within the frequency region over which the optical spectrometer operates.

2. An optical spectrometer, acting upon probe light, comprising:

(a) an absorbing substance;

(b) a longitudinal magnetic field permeating the absorbing substance;

(c) a polarizing beam splitter;

wherein absorption is associated with a transition from a ground state to an excited state of the absorbing substance;

wherein the absorbing substance and the longitudinal magnetic field combine to form a birefringent medium;

wherein the absorbing substance and the longitudinal magnetic field combine to form a first absorption line at a first frequency that absorbs a first circular polarization component of the probe light;

wherein the absorbing substance and the longitudinal magnetic field combine to form a second absorption line at a second frequency that absorbs the first circular polarization component of the probe light;

wherein the first frequency is different than the second frequency;

wherein the probe light propagates through the birefringent medium and then is transmitted through the polarizing beam splitter;

wherein the birefringent medium changes the polarization of the probe light an amount that is dependent upon probe light frequency;

wherein the polarizing beam splitter splits the probe light into a first linear polarization component and a second linear polarization component;

wherein the angular orientation of the polarizing beam splitter relative to the probe light polarization axis is such that the first linear polarization component emerging from the polarizing beam splitter is not an orthogonal component relative to the original polarization orientation of the probe light;

wherein the angular orientation of the polarizing beam splitter relative to the original probe light polarization axis is such that the second linear polarization component emerging from the polarizing beam splitter is not an orthogonal component relative to the original polarization orientation of the probe light;

and probe light frequency is determined from the relative magnitude of the first linear polarization component to the second linear polarization component.

* * * * *